United States Patent [19]

Hester, Jr. et al.

[11] Patent Number: 5,874,475
[45] Date of Patent: Feb. 23, 1999

[54] ANTIARRHYTHMIC (S)-ENANTIOMERS OF METHANESULFONAMIDES

[75] Inventors: Jackson B. Hester, Jr., Galesburg; J. Kenneth Gibson, Kalamazoo, both of Mich.

[73] Assignee: Pharmacia & Upjohn Company, Kalamazoo, Mich.

[21] Appl. No.: 860,531

[22] PCT Filed: Dec. 21, 1995

[86] PCT No.: PCT/US95/16017

§ 371 Date: Jun. 20, 1997

§ 102(e) Date: Jun. 20, 1997

[87] PCT Pub. No.: WO96/21643

PCT Pub. Date: Jul. 18, 1996

[51] Int. Cl.$^6$ .......................... A61K 31/18; C07C 311/08
[52] U.S. Cl. .............................. 514/605; 514/821; 564/99
[58] Field of Search ..................................... 514/605, 821; 564/99

[56] References Cited

U.S. PATENT DOCUMENTS

| | | | |
|---|---|---|---|
| 3,341,584 | 9/1967 | Larsen et al. | 260/556 |
| 3,478,149 | 11/1969 | Larsen et al. | 424/228 |
| 3,574,741 | 4/1971 | Gould et al. | 260/556 |
| 4,507,320 | 3/1985 | DeMarimis et al. | 514/605 |
| 4,569,801 | 2/1986 | Molloy et al. | 260/501.21 |
| 4,596,827 | 6/1986 | Molloy et al. | 514/605 |
| 5,155,268 | 10/1992 | Hester, Jr. | 564/99 |

FOREIGN PATENT DOCUMENTS

| | | |
|---|---|---|
| 0 127 435 | 12/1984 | European Pat. Off. . |
| 0 134 424 | 3/1985 | European Pat. Off. . |
| 0 164 865 | 12/1985 | European Pat. Off. . |
| 0 596 490 A2 | 5/1994 | European Pat. Off. . |
| WO 91/01299 | 2/1991 | WIPO . |

OTHER PUBLICATIONS

Morgan, TK; Wohl, RA; Lumma, WC; Wan, CN; Davey, DD; Gomez, RP; Marisca, AJ; Briggs, M; Sullivan, ME; Wong, SS; Synthesis and Class III antiarrhythic Activity of (Phenylbut–2–enyl)ammonium Salts. Effect of Conformation of Activity, J. Med. Chem., vol. 29, No. 8, 1398–1405 (1986).

Cimini, MG; Brunden, MN; Gibson, JK; Effects of ibutiide fumarate, a novel antiarrhythmic agent, and its enantiomers on isolated rabbit myocardium, European Journal of Pharmacology, 222 (1992) 93–98.

Stolle, WT; Stelzer, LS; Hester, JB; Perricone, SC; Hsi, RSP; Synthesis of radiolabeled racemic and enantiomeric antiarrhythmic agents, Chemical Abstracts, vol. 122, 1995, pp. 1156, 55666.

Primary Examiner—Peter O'Sullivan
Attorney, Agent, or Firm—Donald L. Corneglio; Lucy X. Yang

[57] ABSTRACT

Compounds of formula (I) and pharmacologically acceptable salts thereof wherein: n is 1 to 3, R is an alkyl, $R_1$ is hydrogen or alkyl, $R_2$ is alkyl, $R_3$ is an alkyl; b) alkyl substituted with an aryl, heteroaryl or cycloalkyl; c) alkyl substituted with one to eight fluorine atoms; d) cycloalkyl; e) alkenyl; f) alkyl substituted with one to three hydroxy, acyloxy or alkoxy substituents, and where the sum of carbons in $R_2$ and $R_3$ is greater than five br where $R_2$ and $R_3$ with the nitrogen atom form a saturated heterocyclic group having one nitrogen and form 4–8 carbon atoms or a 4-substituted piperazine group in which the 4-substituent can be alkyl, aryl, benzyl, or heteroaryl, and X is hydrogen, hydroxy, alkoxy, alkyl, carbon trifluoride or a halogen, or compounds of formula (I') and pharmacologically acceptable salts thereof wherein: n is 1 to 3, R is an alkyl, $R_1$ is hydrogen or alkyl, $R_2$ is an alkyl, $R_3$ is an alkyl substituted with an aryl, heteroaryl or cycloalkyl, or an alkyl substituted with one to eight fluorine atoms, one to three hydroxy, acyloxy or alkoxy substituents, and where the sum of carbons in $R_2$ and $R_3$ is greater than five; X is hydrogen, hydroxy, alkoxy, alkyl, carbon trifluoride or a halogen, useful as class III antiarrhythmic agents.

6 Claims, No Drawings

ANTIARRHYTHMIC (S)-ENANTIOMERS OF METHANESULFONAMIDES

BACKGROUND OF THE INVENTION

The present invention is directed toward selected (S)-enantiomeric methanesulfonamides characterized by a hydroxy-alkyl linkage between a tertiary amine group having a substituted side chain and a methanesulfonamide substituted phenyl, useful as Class III antiarrhythmics. These novel enantiomeric methanesulfonamides prolong the effective refractory period of the myocardium and are very potent and stable against metabolism. More importantly, these Class III antiarrhythmic compounds do not have the undesirable side effect of producing polymorphic ventricular tachycardia ("PVT").

Antiarrhythmic drugs act upon the electrophysiological properties of the myocardium and conductive tissues. Typically the rhythmic contractions of the heart are dependent upon the ability of the myocardium and conductive tissues to respond to electrical impulses. When the conductivity of the heart's muscle and conductive tissue is altered by an occlusion of an artery or disease, a life threatening cardiovascular deterioration is likely. It is therefore desirable to treat the electrophysiological properties of the myocardium and conductive tissue to restore rhythmic contractions.

One means for restoring rhythmic contraction is with an antiarrhythmic agent that selectively prolongs the action potential duration and concomitantly increases the refractory period of heart cells without significant effect on cardiac conduction. Such drugs are classified as Class III antiarrhythmic agents. Class III antiarrhythmics which have good bioavailability and which do not affect other circulatory parameters such as blood pressure and heart rate are continually being sought. The subject compounds are Class III antiarrhythmics which are suitable for the treatment of mammals suffering from arrhythmic disorders or disease.

Unfortunately, Class III antiarrhythmic agents are known to produce PVT or torsades de pointes, which is a drug-induced arrhythmia, in a percentage of patients treated with these agents. This potentially lethal arrhythmia represents a liability for this class of antiarrhythmic agents. Surprisingly, it has been discovered that the instant compounds, although potent Class III antiarrhythmics, do not cause PVT in an animal model for this arrhythmia. This is a breakthrough in preparing a Class III antiarrhythmic without the serious PVT side effect.

Bioavailability is an important characteristic of any drug. Unfortunately, with compounds similar to the subject compounds such as those disclosed in U.S. Pat. No. 5,155,268, bioavailability is hampered by a rapid metabolism of the amine side chain. The subject invention solves this problem, as previously disclosed in PCT WO 91/01299, by substituting the side chain with at least one fluorine atom to prevent rapid metabolism and thereby increase bioavailability.

INFORMATION DISCLOSURE STATEMENT

The subject compounds are generally related to those compounds described in European Patent No. 0164865, which can be used as intermediates for the preparation of the subject compounds; and PCT WO 91/01299 which does not disclose the advantageous S-enantiomeric form of the subject compounds.

European Patent Application EP 0134424 discloses quaternary ammonium salts of compounds which are isomers of the subject alkanesulfonamides.

T. K. Morgan, Jr. et al., J. Med Chem., 29, 1398 (1986) reports tertiary amine alkanesulfonamides compounds.

U.S. Pat. Nos. 3,341,584 and 3,478,149 disclose sulfonamide compounds some of which can be used as intermediates for the preparation of the subject compounds.

Other U.S. Patents having examples of sulfonamide containing compounds and antiarrhythmic activity are DeMarinis et al. U.S. Pat. No. 4,507,320, Molloy et al. U.S. Pat. Nos. 4,569,801 and 4,596,827, and Gould et al. U.S. Pat. No. 3,574,741.

SUMMARY OF THE INVENTION

In one aspect the subject invention is directed toward a compound of Formula I, where the asymmetric alcohol carbon has the (S) absolute configuration, its enantiomers at other asymmetric carbons or pharmacologically acceptable salts thereof.

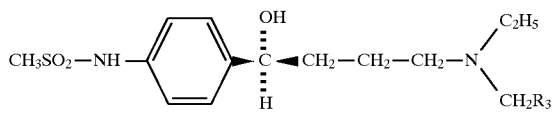

Formula I is defined where $R_3$ is a $C_{1-9}$ alkyl substituted with one fluorine atom.

In another aspect the subject invention is directed toward a method for treating cardiac arrhythmia in mammals comprising the administration of a therapeutically effective amount of a compound of Formula I including pharmacologically acceptable salts thereof. An effective amount is from about 0.01 to about 300 mg. Preferably, the compound is administered in a unit dosage form for oral, sublingual, transdermal or parenteral administration.

The Formula I compounds are generally prepared into pharmaceutical preparations or compositions for therapeutic administration to patients suffering from cardiac arrhythmia. The compounds are classified as Class III antiarrhythmic compounds which are agents that selectively prolong the action potential duration and concomitantly increase the refractory period of heart cells without significant effects on cardiac conduction. Advantageously, Formula I does not cause PVT's.

DETAILED DESCRIPTION OF THE SUBJECT INVENTION (S)-Enantiomeric alkanesulfonanilides which prolong the effective refractory period of the myocardium and are useful for treating cardiac arrhythmias in mammals without the side effect of PVT are disclosed. The compounds of the present invention are represented by the structural Formula I, or its pharmaceutically acceptable salts. Formula I is defined where $R_3$ is a $C_{1-9}$ alkyl substituted with one fluorine atom.

Typically, compounds similar to those described herein suffer from the undesirable side effect of PVT which is eliminated by using the (S)-enantiomeric preparation. Bioavailability is also increased due to the substitutions on the side chain which advantageously prevent rapid metabolism and thereby increase the therapeutic utility of the compounds.

An "alkyl" is a straight or branched carbon chain containing the number of carbon atoms designated such as $C_{1-4}$, $C_{1-5}$, $C_{1-10}$, etc. A "substituted" alkyl is a straight or branched carbon chain having a hydrogen atom replaced by another chemical group such as a fluorine atom.

"Pharmacologically acceptable salts" are acid addition salts which can be prepared by any of the art recognized means. Typical, acid addition salts include hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates, fumarates and other pharmaceutically acceptable counter ions for amines.

The Formula I compounds are used for the treatment of arrhythmia wherever a Class III antiarrhythmic drug is indicated. The compounds and compositions of Formula I are administered in a therapeutically effective amount which is an amount sufficient to control arrhythmia in the host being treated such as mammals which includes humans. Typically, the Formula I antiarrhythmic agents are used in unit dosages of from 0.01 to 300 mg in oral or injectable preparations. Preferably, the Formula I compounds are used in unit dosages of 0.001 to 10 mg/kg for administration by routes either oral, sublingual, transdermal, or parenteral such as by subcutaneous, intramuscular, or intravenous injection.

The particular dose of compound administered according to this invention will of course be determined by the particular circumstances surrounding the case, including the compound administered, the route of administration, the particular arrhythmia being treated, and similar considerations.

The Formula I compounds can be formulated into typical pharmaceutical preparations for either oral or parenteral administration. For example, the Formula I compound can be formulated into a composition by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelation capsules for convenient oral administration.

A gelatin capsule suited to oral administration may contain, for example, a Formula I compound in the amount of about 0.1 to about 100 mg. Such formulation can be administered orally as often as needed depending upon the particular condition and patient being treated.

For parenteral administration a Formula I compound can be formulated for intramuscular or intravenous administration. In the case of treatment of a patient suffering from a severe cardiac arrhythmia, it may be desirable to administer the Formula I compound by intravenous infusion in order to effect a speedy conversion to a normal cardiac rhythm. Such normal condition can then be maintained by oral administration.

The compositions of the present invention may also include sustained release oral dosage forms and controlled release dosage forms by which the effect of the dosage is through the skin. Such compositions are those known to an ordinary skilled artisan or can be ascertained by ordinary experimentation from known compositions such as creams, gels, pastes or liquids. Typical transdermal compounds are polyethylene glycol, triacetin, propylcarbonate, ethanol and isopropyl myristate.

The Formula I compounds can be combined with other antiarrhythmic agents having the same or different mechanisms of action. For example, combinations may include, Class I antiarrhythmic agents, such as quinidine, tocainide, lidocaine or the like; Class II antiarrhythmic agents, such as, propranolol, sotalol, atenolol or the like; Class III antiarrhythmic agents such as clofilium, sotalol, amiodarone and meobentine; and Class IV antiarrhythmic agents such as verapamil or diltiazem.

Formula I compounds as shown in Examples 1, 2 and 3 are prepared as follows. Examples of suitable starting materials are described in European Patents 0 164 865 and 0 233 051, U.S. Pat. Nos. 3,341,584, 3,478,149 all herein incorporated by reference.

According to Scheme 1, in Step I, (4-methanesulfonylamino)-γ-oxobenzenebutanoic acid (II, prepared as described in EP 164 865) is converted to the N-ethylamide (III). Standard amide forming reagents such as dicyclohexylcarbodiimide or preferably isobutyl chloroformate can be used for this purpose. In Step II the ketone of III is reduced with the chiral reagent (-)-B-chlorodiisopinocamphenylborane in tetrahydrofuran. The reaction is carried out below 0° C. and preferably at −25° to −35° C. A nonaqueous work up is used to facilitate isolation of the water soluble product. The (S)-(-) enantiomer of the chiral alcohol is obtained. Purification of this alcohol by recrystallization from acetonitrile, methanol, ethanol, tert-butyl methyl ether or mixtures thereof gives IV with high enantiomeric purity. In Step III the amide of IV is reduced with sodium bis-(2-methoxyethoxy)aluminum hydride in tetrahydrofuran at 24° C. A neutral nonaqueous work up is employed to facilitate isolation of the water soluble product (V). Alkylation of V with appropriately substituted alkyl bromides ($R_3CH_2Br$) to give the compounds (I) of this invention is accomplished in Step IV. The preferred conditions for this reaction employ acetonitrile as solvent and the weakly basic sodium bicarbonate to neutralize the hydrogen bromide generated by the reaction. The reaction is usually carried out at the reflux temperature (81° C.).

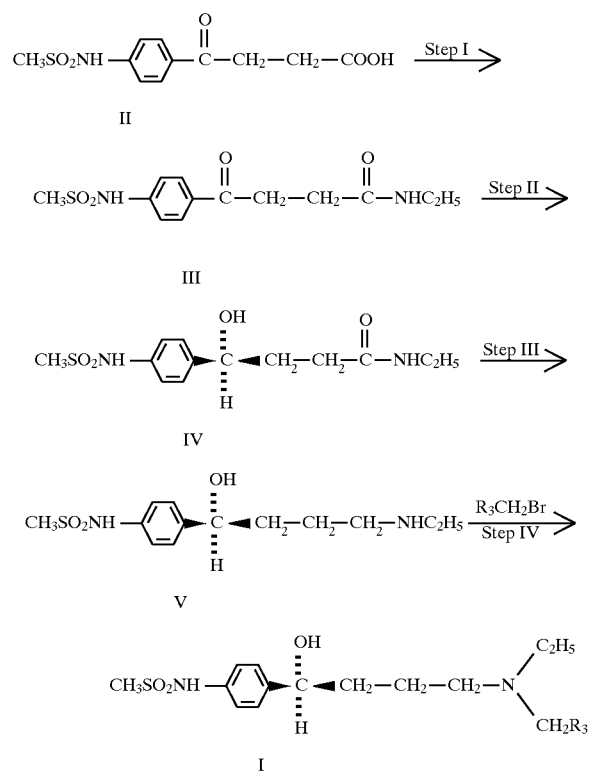

The Formula I compounds were evaluated for electrophysiological activity in an isolated, perfused rabbit cardiac tissue system. The method used was as follows:

New Zealand White rabbits of either sex (1.5–2.0 kg) were anesthetized and their hearts removed. The heart was immersed in ice cold perfusate while the right atria (RA), papillary muscles (PAP), and right ventricular muscle strips (RV) were isolated. The perfusate was continuously oxygenated with 95% oxygen and 5% carbon dioxide and contained the following in mM concentrations: NaCl 118.0; KCl 5.4; NaHCO$_3$ 25.0; MgCl$_2$ 1.2; KH$_2$PO$_4$ 1.0; CaCl$_2$ 2.4; glucose 110.0 and pyruvic acid 2.0. During hypoxic conditions the perfusate was exposed to a mixture of 83% nitrogen, 10% carbon dioxide and 7% oxygen. The pH during normoxia was approximately 7.4 and dropped to approximately 7.2 during hypoxic conditions.

The tissues were individually mounted on a plexiglass holder containing platinum stimulating electrodes and suspended in a 100 ml bath maintained at 30° C. by a circulating heat pump. All tissues were attached by silk suture to a force-displacement transducer and a tissue-dependent preload of 500–1000 mg was applied. RA were allowed to contract spontaneously. RV and PAP were stimulated at 2× threshold with 4 msec rectangular pulses at a frequency of 1 and 3 Hz. (Effective refractory period measurements percent increment over control are ERP1 and ERP3, conduction time measurements are CT1 and CT3). Between measurements those tissues were stimulated at a resting pace of 2 Hz. Each tissue served as its own baseline control and was allowed an equilibration period of two hours prior to experiments. During this period the perfusate was changed every 10–15 minutes.

Working solutions of the drugs were prepared by dissolving the drugs in distilled water and one drop of NaOH/ml to aid in dissolution (pH 9.4).

Measurements were made on each set of tissues after exposure to $10^{-7}$, $10^{-6}$, or $10^{-5}$M drug for 15 minutes: and $10^{-5}$M drug under hypoxic conditions for 15 minutes.

Automaticity (RATE), force of contraction (FOC) and threshold were measured directly on a polygraph. The ERP of cardiac tissues by definition is the longest coupling interval between the basic drive (S1) and the premature impulse (S2) that fails to propagate through the tissue. The S2 stimulus was introduced after every eighth S1 which allowed time for stabilization of refractoriness. Refractory period measurements were made via a digital timing circuit. The limit of resolution for these refractory period measurements was approximately 6 msec. Conduction time measurements (CT) were recorded directly in msec by gently placing a teflon-coated silver bipolar electrode against the endocardial surface of the RV strip with the resulting electrocardiogram displayed on an oscilloscope. An increase in CT is equivalent to a decrease in conduction velocity.

Examples of Formula I compounds evaluated in this manner are collected in Table I. A measure of the class III antiarrhythmic activity of these compounds is indicated by the percent increase in the effective refractory period of rabbit papillary muscle determined at pacing rates of 1 and 3 Hz (ERP$_1$ and ERP$_3$). The corresponding data for ibutilide, a compound of U.S. Pat. No. 5,155,268 is shown for comparison.

The Formula I compounds were evaluated for their ability to produce early after depolarizations (EAD) and polymorphic ventricular tachycardia (PVT) in methoxamine treated rabbits. The method used was as follows:

Male New Zealand White rabbits (2.5–3.5 kg,) pretreated with subcutaneous morphine sulfate (5 mg/kg) 30 minutes prior to anesthesia. Anesthesia was induced by infusion of α-chloralose (90–120 mg/kg) through a marginal ear vein over a period of 20 to 30 minutes. A tracheotomy was performed and the rabbit was respirated with room air (5–6 cc/kg) using a small animal ventilator (Columbus Instruments, Columbus, Ohio). Respiration rate, and tidal volume were adjusted, and supplemental oxygen administered to maintain arterial blood gases and pH within normal physiologic ranges. Catheters were placed in a jugular vein and carotid artery for administration of drugs, and measurement of arterial blood pressure, respectively. A 4 French monophasic action potential catheter was introduced through a jugular vein for monitoring of right ventricular monophasic action potential duration which was measured at 90% repolarization (MAPD$_{90}$). A lead II ECG and arterial blood pressure were monitored throughout the experiments.

All records were obtained on a multichannel recorder (Gould ES 2000, Cleveland, Ohio) and experiments were continuously recorded on FM magnetic tape (TEAC 501, Montebello, Calif.) for subsequent playback and analysis.

Following experimental preparation, the rabbits were allowed to equilibrate for 10 minutes before baseline measurements of heart rate, aortic blood pressure, and QTc interval were made. During the equilibration period, monophasic action potentials were monitored and the catheter adjusted to produce action potentials with a stable amplitude. Following baseline measurements, the α$_1$ agonist methoxamine was infused at a rate of 10 μg/kg/minute at an infusion volume of 12.0 ml/hr. After 15 minutes of methoxamine administration, intravenous infusion of saline (vehicle control) or a class III agent was begun. All agents were administered as a continuous infusion over a 1 hour period. Measurement of heart rate, aortic blood pressure, QTc interval (as defined below), and MAPD$_{90}$ were repeated at several time points during drug administration to provide dose-response relationships. QTc and MAPD$_{90}$ were also monitored to insure that maximal class III effects on these parameters had been achieved.

Total accumulated dose at the first incidence of PVT was also measured. Repolarization arrhythmias were characterized as early after depolarizations and extrasystoles during repolarization which produced extrasystoles in lead II ECG. PVT was considered to have occurred if 3 or more closely coupled repetitive extrasystoles with a twisting or torsioning QRS morphology were observed.

Methoxamine HCl, and α-chloralose were purchased from Sigma Chemical Company, St. Louis, Mo. Morphine sulfate was obtained from the Eli Lilly Co., Indianapolis, Ind.

QT intervals were corrected for heart rate changes using the formula QTc=QT/square root R—R interval. EADs were compared between treatment groups at stable monophasic action potential amplitudes (APA) and are reported as a percent of the APA.

Examples of Formula I compounds evaluated in this manner are collected in Table II. A measure of Class III antiarrhythmic activity is indicated by an increase in QTc and MAPD$_{90}$. The proarrhythmic potential is indicated by the incidence and magnitude of the EADs and by the ratio of the incidence of PVT to the total number of animals tested. The corresponding data for ibutilide, a compound of U.S. Pat. No. 5,155,268, and the racemc forms Examples (R,S) (compounds of PCT WO 91/01299) are shown for comparison.

TABLE 1

| Example # | R$_3$ | ERP$_1$* (SE)[1] | | ERP$_3$** (SE)[1] | |
|---|---|---|---|---|---|
| 1 | (CH$_2$)$_5$—CH$_2$F | 43.5 | (18.5) | 26.1 | (21.3) |
| 2 | (CH$_2$)$_4$CH(F)CH$_3$ | 30.7 | (8.8) | 8.7 | (8.9) |

TABLE 1-continued

| Example # | R₃ | ERP₁* (SE)[1] | | ERP₃** (SE)[1] | |
|---|---|---|---|---|---|
| 3 | (CH₂)₄C(CH₃)₂F | 21.4 | (3.9) | 25.4 | (13.7) |
| Ibutilide[2] | (CH₂)₆CH₃ | 18.0 | (4.1) | 15.8 | (2.0) |

*percent increase in the effective refractory period over control values measured at a drug concentration of $10^{-5}$ M and a pacing rate of 1 Hz
**percent increase in the effective refractory period over control values measured at a drug concentration of $10^{-5}$ M and a pacing rate of 3 Hz
[1]Standard error of the mean
[2]Not a compound of the invention, U.S. Pat. No. 5.155.268

TABLE 2

| Ex. No. | QTc[a] | MAPD₉₀[c] | EAD[d] | PVT[e] |
|---|---|---|---|---|
| 1 | +112(1)[b] | +70(1)[b] | 0 | 0/16 |
| 2 | +119(0.25) | +88(1) | 0 | 0/16 |
| 3 | +82(1) | +75(3) | 0 | 0/16 |
| (R,S) 1[g] | +143(0.5) | +128(1) | 52(0.5)[b] | 1/6(2)[f] |
| (R,S) 2[h] | +166(0.25) | +141(0.25) | 63(1) | 3/6(0.2) |
| (R,S) 3[i] | +136(0.25) | +96(1) | 35(0.25) | 1/6(0.2) |
| ibutilide[j] | +95(10) | +114(10) | 15(4) | 2/16(1) |

[a]Maximum increase in QTc interval (m sec) from the methoxamine infusion baseline.
[b]Total accumulated dose (mg/kg) of test compound when this value was measured.
[c]Maximum increase in the ventricular monophasic action potential duration (m sec), from the methoxamine infusion baseline, measured at 90% repolarization.
[d]Magnitude of the maximum early after depolarization amplitude as a percent of the monophasic action potential amplitude (APA).
[e]Ratio of the number of animals that developed polymorphic ventricular tachycardia to the total number of animals evaluated.
[f]Total accumulated dose at the first incidence of PVT.
[g]Racemic form of Example 1 for comparison not a compound of this invention.
[h]Racemic form of Example 2 for comparison, not a compound of this invention.
[i]Racemic form of Example 3 for comparison, not a compound of this invention.
[j]Compound for comparison, not a compound of this invention.

EXAMPLE 1

(S)-(-)-N-[4-[4-[Ethyl(7-fluoroheptyl)aminol]-1-hydroxybutyl]phenyl] methanesulfonamide, (E)-2-Butenedioate (2:1 salt)

Step I. N-Ethyl-γ-oxo-4-(methanesulfonylamino) benzenebutanamide

A stirred suspension of 4-((methanesulfonyl)amino)-γ-oxobenzenebutanoic acid (described in EP 164 865) (20 g, 0.0737 mol) in THF (600 ml) was treated with 13.7 ml (0.098 ml) of triethylamine and cooled to −12° C. in an ice-methanol bath. This mixture was treated dropwise with isobutyl chloroformate (12.7 ml, 0.098 mol) and kept at −12° C. for 1.5 hours. A solution of ethylamine (4 g, 0.089 mol) and triethylamine (13.7 ml, 0.098 mol) in THF (173 ml) was then added dropwise. The mixture was kept at −12° C. for 3 hours and poured into 780 ml of ice-cold 1 N HCl. Nitrogen was bubbled through this mixture to remove the THF. The solid was collected by filtration washed with aqueous NaHCO₃ and water and dried in vacuo to give 14.27 g of crude product. Additional product (4 g) was obtained by extracting the acid filtrate with EtOAc. The combined product was washed with MeOH and dried to give 13.75 g of N-ethyl-γ-oxo-4-((methanesulfonyl)amino) benzenebutanamide. The analytical sample was recrystallized from acetonitrile and had mp 210°–213° C. Anal. calc'd for $C_{13}H_{18}N_2O_4S$: C, 52.34; H, 6.08; N, 9.39; S, 10.75. Found: C, 52.02; H, 6.26; H, 9.28; S, 10.63.

Step II. (S)-(-)-N-Ethyl-γ-hydroxy-4-(methanesulfonylamino)benzenebutanamide

A stirred solution of the product from Step I (490.1 g, 1.64 mol) in THF (4 L), under nitrogen, was cooled to −30° to −35° C. and treated during 1.5 hours with a solution of (-)-B-chlorodiisopinocampheylbovane (920 g, 2.86 mol) in THF (2 L). The mixture was stirred at −25° C. for 3.5 hours when the reaction was complete by TLC with 10% MeOH—CH₂Cl₂ on silica gel. It was then treated with diethanolamine (600 ml) while it was warmed to 0° C. This mixture was kept at 0°–10° C. for 10 minutes and at ambient temperature (24° C.) for 18 hours. The resulting mixture was concentrated to a slurry while adding MeOH to displace the residual solvent. The concentrate was mixed with MeOH and washed with heptane. The MeOH solution was concentrated to an oil which was chromatographed on silica gel with mixtures of MeOH and CH₂Cl₂ containing 0–10% MeOH. A solution of the resulting product in acetonitrile was mixed with tert-butyl methyl ether and allowed to crystallize at 0° C. to give the titled product: mp 137°–138° C.; $[α]_D^{24}$ −16° (c 0.95, EtOH);
Anal. Calc'd for $C_{13}H_{20}N_2O_4S$: C, 51.98; H, 6.71; N, 9.33; S, 10.68.
Found: C, 51.88; H, 6.82; N, 9.10; S, 10.53.

The chiral purity of the titled product was determined by first allowing a sample in acetonitrile to react with 1-naphthylisocyanate and then analyzing the derivatized product by HPLC on a Pirkle covalent D-phenylglycine column. It was 99.5% pure (-) enantiomer.

Step III. (S)-(-)-N-[4-[4-(Ethylamino)-1-hydroxybutyl]phenyl]methanesulfonamide

A 65% solution of sodium bis(2-methoxyethoxy) aluminum hydride in toluene (44 ml, 0.146 mol) was mixed with THF (100 ml) under nitrogen and the stirred mixture was treated, portionwise during 2 hours, with a suspension of the product from Step II (11.45 g, 0.0381 mol) in THF (360 ml). An exothermic reaction increased the temperature of the reaction mixture to 34° C. during this addition. The mixture was kept at ambient temperature (24° C.) for 18 hours, cooled to 8° C. and treated, dropwise during 10 minutes, with 6M H₂SO₄ (3 ml). The cooling bath was removed and the mixture was treated with additional 6M H₂SO₄ (19 ml) during 2 hours; the pH of the mixture was 10. This mixture was treated with MeOH (150 ml) and stirred for 2.5 hours. The solid was collected by filtration and washed with 10% MeOH—CH₂Cl₂ (800 ml). The combined filtrate was concentrated and the residue crystallized from EtOH to give 5.28 g of the titled product: mp 168°–170° C.; $[α]_D$ −20° (C 0.85, MeOH);
Anal. Calc'd for $C_{13}H_{22}N_2O_3S$; C, 54.51; H, 7.74: N, 9.78: S, 11.20.
Found: C, 54.32; H, 7.52; N, 9.96: S, 11.05.

Step IV. 1-Bromo-7-fluoroheptane

A stirred solution of 7-bromo-1-heptanol (1.53 g, 7.85 mmol) in 2.5 mL of CCl₄ was cooled in an ice bath, under nitrogen, and treated with 2.25 mL (17.0 mmol) of DAST; the flask was stoppered with a teflon stopper and secured with a plastic clip. The mixture was stirred in the cold 30 min and, after removing the ice bath, at ambient temperature. After 4.5 h an aliquot was assayed by TLC to show unreacted starting material; 0.7 mL (5.3 mmol) more of the DAST was added, the flask stoppered and stirred at room temperature overnight. The resultant mixture was added dropwise to 25 mL of ice/water over 5 min and this was extracted with hexane. The organic extracts were washed sequentially with water, 10% aqueous Na₂CO₃, and brine. The pooled extract was dried (MgSO₄) and concentrated.

The residue was chromatographed under pressure over 300 mL of silica gel (230–400) mesh with 4% $CH_2Cl_2$/hexane to give 0.9 g (53%) of product, 1-bromo-7-fluoroheptane: NMR ($CDCl_3$) δ1.43 (m, 6H), 1.71 (m, 2H), 1.87 (m, 2H), 3.42 (t, 2H), 4.37, 4.52 (t's, 2H).

Step V. (S)-(-)-N-[4-[4-[Ethyl(7-fluoroheptyl)amino]-1-hydroxybutyl]phenyl]-methanesulfonamide, (E)-2-Butenedioate (2:1 salt)

A stirred mixture of the product from Step III (2.58 g, 0.009 mol), the product from Step IV (2.0 g, 0.01 mol), powdered $NaHCO_3$ (1.68 g, 0.02 mol) and acetonitrile (80 ml) was refluxed under nitrogen for 18 hours and then concentrated in vacuo. A mixture of the residue and water was extracted with EtOAc. The extract was washed with water and brine, dried ($MgSO_4$) and concentrated. The residue was chromatographed on silica gel with 6% MeOH–0.3% $NH_4OH$—$CHCl_3$. A solution of the product thus obtained in EtOAc was washed with water and brine, dried ($MgSO_4$) and concentrated to give 1.92 g (0.00476 mol) of (S)-(-)-N-[4-[4-[Ethyl(7-fluoroheptyl)amino]-1-hydroxybutyl]phenyl]methanesulfonamide. A solution of this material in acetone was mixed with 0.276 g (0.00238 mol) of fumaric acid and the resulting salt was crystallized from acetone to give 1.78 g of the titled product: mp 126°–127° C.; $[\alpha]_D$-15° (c 1.0, EtOH);

Anal. Calc'd for $C_{22}H_{37}FN_2O_5S$: C, 57.36; H, 8.10; N, 6.08; S, 6.96.

Found: C, 57.30; H, 8.08; N, 5.94; S, 6.94.

EXAMPLE 2

(S)-(-)-N-[4-[4-[Ethyl(6-fluoroheptyl)amino]-1-hydroxybutyl]phenyl]-methanesulfonamide, (E)-2-Butenedioate (2:1 salt)

Step I. 6-Hydroxyheptanoic acid, ε-lactone

A solution of 2-methylcyclohexanone (11.1 g, 0.099 mol) in chloroform (15 ml) was added during 20 minutes, under nitrogen, to a stirred suspension of m-chloroperbenzoic acid (24.6 g, 0.143 mol) in chloroform (250 ml). After 3 hours, 40 minutes, the mixture was poured into aqueous sodium bicarbonate and extracted with methylene chloride. The extract was washed with brine, dried ($MgSO_4$) and concentrated. The residue was distilled from a small amount of $K_2CO_3$ to give 9.58 g, bp 78°–79° C. (2.5–3 mm Hg) of 6-hydroxyheptanoic acid, ε-lactone.

Step II. Ethyl-6-hydroxyheptanoate

A solution of 6-methyl-ε-caprolactone, the product from Step I (18.94 g, 0.148 mol) in 65 mL of absolute EtOH was treated with 0.8 mL of conc. $H_2SO_4$, stirred at room temperature for 7 hours and concentrated in vacuo. The residue was treated with ice and neutralized with dilute $NaHCO_3$. The aqueous mixture was extracted with $Et_2O$ and the extracts were washed with water and then brine. The pooled extract was dried ($MgSO_4$) and concentrated to give 24.38 g of crude product. This was combined with the product from a previous reaction and distilled to give 18.45 g, bp 96° C. (2.2 mm Hg) and 6.73 g, bp 91° C. (0.8 mm Hg) of the titled product.

Step III. Ethyl 6-fluoroheptanoate

A solution of the product from Step II (18.4 g, 0.106 mol) in 200 mL of $CH_2C_2$, under nitrogen, was cooled to −72° C. in a dry ice-acetone bath and treated dropwise with a solution of 30 mL (0.225 mol) of $Et_2NSF_3$ (DAST) in $CH_2Cl_2$ (195 ml) over 1 hour. The mixture was stirred at −72° C. for 1 hour and then for 2 hours while the mixture was allowed to warm to 5° C. (by periodic addition of acetone to the bath). The mixture was maintained at 5° C. for 15 minutes then poured into a mixture of 600 mL of 10% $Na_2CO_3$ and 200 mL of ice with vigorous swirling (foaming). The pH of the resulting aqueous mixture was 7. This was extracted with $Et_2O$; the extracts were washed with water and brine, dried ($MgSO_4$) and concentrated. The residue was distilled to give 7.16 g (38.5%) of the titled product, bp 76°–78° (5.8 mm Hg): NMR ($CDCl_3$) δ 1.26 (m, 4.5H), 1.35 (d, 1.5H), 1.57 (m, 6H), 2.32 (t, 2H), 4.13 (q, 2H), 4.57, 4.72 (m's, 1H).

Step IV. 6-Fluoro-1-heptanol

To a mixture of 3.64 g (0.096 mol) of $LiAlH_4$ in 200 mL of $Et_2O$, under $N_2$, at 4° C. was added a solution of the product from Step III (10.4 g, 0.059 mol) in 35 mL of $Et_2O$ over 45 minutes. The mixture was stirred in the cold for 15 minutes and allowed to warm to room temperature over 100 minutes. The mixture was cooled in an ice bath and treated dropwise during 40 minutes with 35 mL of saturated aqueous $Na_2SO_4$; 200 mL more $Et_2O$ was added and after stirring at ambient temperature for 15 minutes the mixture was filtered through a pad of $Na_2SO_4$. The filter cake was washed well with $Et_2O$ and the filtrate was concentrated in vacuo. The residue was distilled to give 4.8 g (60.7%) of the titled product, bp 85°–87° C. (9.2 mm Hg), which by NMR was slightly contaminated by an alkene, and 0.58 g (7.3%) of clean product; bp 85°–87° C. (9.2 mm Hg); NMR ($CDCl_3$) δ 1.27, 1.35 (d's, 3H), 1.55 (m, 9H), 3.65 (t, 2H), 4.58, 4.73 (m's, 1H).

Step V. 1-Bromo-6-fluoroheptane

A solution of triphenylphosphine (10.32 g,0.0393 mol) and the product from Step IV (4.8 g, 0.0358 mol) in 75 mL of benzene, under nitrogen, was cooled in an ice bath and treated, in portions over 40 minutes with 7.0 g (0.0393 mol) of N-bromosuccinimide. The mixture was stirred in the cold for 20 minutes and at ambient temperature for 2.5 hours. This mixture was poured into 250 mL of pentane, a precipitate was filtered off and the filtrate was concentrated at ambient temperature in vacuo. The residue was treated with 300 mL of pentane, the mixture was cooled, a solid was filtered off and the filtrate was concentrated to 100 mL. This was cooled and a solid was filtered off. The filtrate was concentrated at ambient temperature in vacuo. The residue was treated with 200 mL of $Et_2O$ and the solution was washed with 5% $Na_2S_2O_3$, 0.5N NaOH and then brine, dried ($MgSO_4$) and concentrated in vacuo at ambient temperature to give 6.6 g (93.6%) of the titled product: NMR ($CDCl_3$) δ 1.22, 1.28 (d's, 3H). 1.57 (m, 6H), 1.88 (m, 2H), 3.42 (t, 2H), 4.57, 4.73 (m's, 1H).

Step VI. (S)-(-)-N-[4-[4-[Ethyl(6-fluoroheptyl)amino]-1-hydroxybutyl]phenyl] methanesulfonamide, (E)-2-Butenedioate (2:1 salt)

A stirred mixture of the product from Example 1, Step III (2.58 g, 0.009 mol), the product from Step V (2.0 g, 0.01 mol), powdered $NaHCO_3$ (1.68 g, 0.02 mol) and acetonitrile (80 ml) was refluxed under nitrogen for 18 hours and concentrated in vacuo. The residue was mixed with water and extracted with EtOAc. The extract was washed with water and brine, dried ($MgSO_4$) and concentrated. The residue was chromatographed on silica gel with 6% MeOH–0.3% $NH_4OH$—$CHCl_3$. A solution of the resulting product in EtOAc was washed with saturated $NaHCO_3$, water and brine, dried ($MgSO_4$) and concentrated to give 1.79 g (0.00443 mol) of (S)-(-)-N-[4-[4-[ethyl(6-fluoroheptyl)amino]-1-hydroxybutyl]phenyl] methanesulfonamide. A solution of this material in acetone was mixed with 0.257 g (0.00222 mol) of fumaric acid and the salt was crystallized from acetone to give 1.26 g of the titled product: mp 108°–111° C.; $[\alpha]_D$ −14° (c 1.0, EtOH);

Anal. Calc'd for $C_{22}H_{37}FN_2O_5S$: C, 57.36; H, 8.10: N, 6.08: S, 6.96.

Found: C, 57.27; H, 8.08; N, 6.02; S, 6.90.

EXAMPLE 3

(S)-(-)-N-[4-[4-[Ethyl(6-fluoro-6-methylheptyl)amino]-1-hydroxybutyl]phenyl]-methanesulfonamide Step I. 5-Chloropentyl 2-tetrahydropyranyl ether A stirred solution of pentamethylene chlorohydrin (10.0 g, 0.0816 mol) in Et$_2$O (165 ml) under nitrogen was treated with 3,4-dihydro-2H-pyran (10.3 g, 0.122 mol) and p-toluenesulfonic acid hydrate (0.5 g) and kept at ambient temperature for 4.5 hours. The mixture was washed with aqueous NaHCO$_3$ and brine, dried (MgSO$_4$) and concentrated. The residue was distilled to give 4.06 g, bp 79°–82° C. (0.1–0.07 mm Hg) and 10.54 g, bp 82°–84° C. (0.1–0.07 mm Hg) of 5-chloropentyl 2-tetrahydropyranyl ether.

Step II. 6-Hydroxy-6-methylheptyl 2-tetrahydropyranyl ether

A small portion of a solution of the product from Step I (21.1 g 0.102 mol) in THF (105 ml) was added, under nitrogen, to magnesium turnings (5.0 g, 0.204 g-atom). The mixture was warmed in an oil bath at 75°–80° and the reaction was started by the addition of 1.5 ml of a 1M solution of 1,2-dibromoethane in THF. The remaining chloroalkane solution was then added during 20 minutes. The resulting mixture was refluxed for 45 minutes, cooled in an ice bath and treated during 15 minutes with a solution of acetone (9.0 ml, 0.123 ml) in THF (95 ml). It was kept at ambient temperature for 16 hours, cooled in an ice bath and treated during 15 minutes with saturated aqueous NH$_4$Cl (115 ml). The resulting mixture was extracted with EtO. The extract was washed with water and brine, dried (MgSO$_4$) and concentrated to give 30.5 of crude product. Distillation gave 16.77g of 6-hydroxy-6-methylheptyl 2-tetrahydropyranyl ether, bp 107°–115° (0.07–0.1 mm Hg). The CI mass spectrum had m/z 231 (M+H)$^+$.

Step III. 6-Fluoro-6-methylheptyl 2-tetrahydropyranyl ether

A solution of the product from Step II, (3.97 g, 0.0173 mol) in CH$_2$Cl$_2$ (12 ml) was added under nitrogen, during 4.5 minutes to a stirred solution of diethylaminosulfur trifluoride (4.6 ml, 0.0345 mol) in CH$_2$Cl$_2$ (12 ml) that had been cooled in a dry ice acetone bath (-78° C.). The mixture was kept in the bath for 15 minutes, warmed to 0° during 10 minutes and mixed with 10% aqueous Na$_2$CO$_3$ (60 ml). This mixture was extracted with CH$_2$Cl$_2$. The extracts were washed with water, dried (MgSO$_4$) and concentrated. The residue was chromatographed on silica gel with 0.05% Et$_3$N-2.5% EtOAc-hexane to give 3.36 g of 6-fluoro-6-methylheptyl 2-tetrahydropyranyl ether.

Step IV. 6-Fluoro-6-methyl-1-heptanol

A stirred solution of the product from Step III (3.34 g, 0.0144 mol) in absolute EtOH was treated with pyridinium p-toluenesulfonate (0.47 g, 0.00187 mol) and kept under nitrogen at ambient temperature for 41 hours. The mixture was concentrated and the residue, dissolved in EtOAc, was washed with aqueous NaHCO$_3$ and brine, dried (MgSO$_4$) and concentrated. The residue was chromatographed on silica gel with 5 to 20% EtOAc-hexane to give 1.86 g of 6-fluoro-6-methyl-1-heptanol.

Step V. 1-Bromo-6-fluoro-6-methylheptane

A stirred solution of the product from Step IV (0.427 g, 0.00288 mol) in benzene (5.2 ml) was mixed with triphenylphosphine (0.83 g, 0.00317 mol) cooled in an ice bath and treated, portion-wise, during 26 minutes with N-bromosuccinimide (0.56 g, 0.00317 mol). The mixture was kept in the ice bath for 30 minutes and at ambient temperature for 3.5 hours; it was then diluted with pentane (20 ml), cooled in an ice bath for a few minutes and filtered. The solid was washed with pentane and the filtrate was concentrated. A mixture of the residue and pentane was cooled in an ice bath for a few minutes and again filtered. The filtrate was mixed with Et$_2$O and washed successively with cold 5% aqueous sodium thiosulfate, 0.5 N NaOH and brine, dried (MgSO$_4$) and concentrated. The residue was chromatographed on silica gel with 1–3% EtOAc-hexane to give 0.440 g of 1-bromo-6-fluoro-6-methylheptane.

Step VI. (S)-(-)-N-[4-[4-[Ethyl(6-fluoro-6-methylheptyl)amino]-1-hydroxybutyl]phenyl-methanesulfonamide A stirred mixture of the product from Example 1, Step III (2.0 g, 0.00698 mol), the product from Step V (1.62 g, 0.00768 mol), sodium bicarbonate (1.17 g, 0.0140 mol) and acetonitrile (60 ml) was refluxed, under nitrogen for 16 hours, cooled and filtered. The filtrate was concentrated in vacuo and the residue was chromatographed on silica gel with 5% MeOH–0.5% NH$_4$OH—CH$_2$Cl$_2$ to give 2.42 g of the titled product, an oil. The high resolution FAB mass spectrum had (M+H)$^+$ at m/z 417. Theory for C$_{21}$H$_{38}$FN$_2$O$_3$S: 417.2587; measured: 417.2602.

We claim:

1. An (S) enantiomeric compound of Formula I

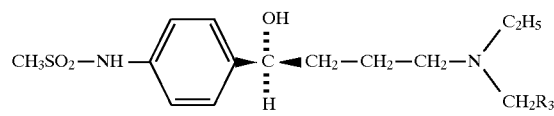

or pharmacologically acceptable salts thereof wherein:

R$_3$ is a C$_{1-9}$ alkyl substituted with one fluorine atom.

2. The compound of claim 1 where R$_3$ is a C$_{5-9}$ alkyl substituted with one fluorine atom.

3. The compound of claim 1 which is:

a) (S)-(-)-N-[4-[4-[Ethyl(7-fluoroheptyl)amino]-1-hydroxybutyl]phenyl]methanesulfonamide, (E)-2-Butenedioate (2:1 salt);

b) (S)-(-)-N-[4-[4-[Ethyl(6-fluoroheptyl)amino]-1-hydroxybutyl]phenyl]methanesulfonamide, (E)-2-Butenedioate (2:1 salt); or c) (S)-(-)-N-[4-[4-[Ethyl(6-fluoro-6-methylheptyl)amino]-1-hydroxybutyl]phenyl]-methanesulfonamide.

4. A method of treating cardiac arrhythmia in patients comprising administering a therapeutically effective amount of a compound of Formula I or pharmaceutically acceptable salts thereof.

5. The method of claim 4 where said effective amount is from about 0.01 to about 300 mg.

6. The method of claim 4 where said compound is in a unit dosage form for oral, sublingual, transdermal or parenteral administration.

* * * * *